(12) United States Patent
Hartwell et al.

(10) Patent No.: US 12,201,764 B2
(45) Date of Patent: Jan. 21, 2025

(54) FLUID COLLECTION

(71) Applicant: Smith & Nephew PLC, Watford (GB)

(72) Inventors: Edward Yerbury Hartwell, Hull (GB); Jonathan Chappel, York (GB); Neill Philip Bannister, Holme on Spanding Moor (GB)

(73) Assignee: Smith & Nephew PLC, Watford (GB)

( * ) Notice: Subject to any disclaimer, the term of this patent is extended or adjusted under 35 U.S.C. 154(b) by 408 days.

(21) Appl. No.: 17/497,657

(22) Filed: Oct. 8, 2021

(65) Prior Publication Data

US 2022/0133977 A1    May 5, 2022

Related U.S. Application Data

(63) Continuation of application No. 16/118,198, filed on Aug. 30, 2018, now Pat. No. 11,141,520, which is a
(Continued)

(30) Foreign Application Priority Data

Feb. 27, 2008    (GB) ...................................... 0803564

(51) Int. Cl.
*A61M 27/00* (2006.01)
*A61M 1/00* (2006.01)

(52) U.S. Cl.
CPC ................ *A61M 1/71* (2021.05); *A61M 1/60* (2021.05); *A61M 1/604* (2021.05); *A61M 1/64* (2021.05);
(Continued)

(58) Field of Classification Search
CPC .......... A61M 1/00; A61M 5/178; A61M 5/00; A61M 5/32; A61M 35/00; A61M 1/0001;
(Continued)

(56) References Cited

U.S. PATENT DOCUMENTS

| 730,062 A | 6/1903 | Widmer |
| 2,468,445 A | 4/1949 | Kenneth et al. |

(Continued)

FOREIGN PATENT DOCUMENTS

| CN | 2623320 Y | 7/2004 |
| DE | 3935818 A1 | 5/1991 |

(Continued)

OTHER PUBLICATIONS

Bevan D., et al., "Diverse and potent activities of HGF/SF in skin wound repair," Journal of Pathology, vol. 203, 2004, pp. 831-838.
(Continued)

*Primary Examiner* — Catharine L Anderson
*Assistant Examiner* — Lynne Anderson
(74) *Attorney, Agent, or Firm* — Knobbe, Martens, Olson & Bear, LLP

(57) ABSTRACT

An apparatus and method for collecting fluid are disclosed. The apparatus includes a body portion comprising a fluid inlet and an outlet, an expandable container secured to the body portion, at least one wicking element extending from within the body portion into the container, and at least one super absorber element arranged inside the container.

7 Claims, 2 Drawing Sheets

Related U.S. Application Data continuation of application No. 14/948,117, filed on Nov. 20, 2015, now Pat. No. 10,071,190, which is a continuation of application No. 12/918,202, filed as application No. PCT/GB2009/050200 on Feb. 27, 2009, now Pat. No. 9,205,183.

(52) U.S. Cl.
CPC ............... *A61M 1/69* (2021.05); *A61M 1/88* (2021.05); *A61M 1/884* (2021.05); *A61M 1/98* (2021.05); *A61M 2205/75* (2013.01)

(58) Field of Classification Search
CPC .... A61M 1/0003; A61M 1/0023; A61M 1/71; A61M 1/60; A61M 1/604; A61M 1/64; A61M 1/69; A61M 1/88; A61M 1/884; A61M 1/98; A61M 2205/75; A61M 1/62; A61F 13/00; A61F 13/05; A61F 5/4401
See application file for complete search history.

(56) References Cited

U.S. PATENT DOCUMENTS

| | | |
|---|---|---|
| 3,572,340 A | 3/1971 | Lloyd et al. |
| 3,980,166 A | 9/1976 | De Feudis |
| 4,063,556 A | 12/1977 | Thomas et al. |
| 4,117,551 A | 9/1978 | Brooks et al. |
| 4,136,696 A | 1/1979 | Nehring |
| 4,203,445 A | 5/1980 | Jessup et al. |
| 4,228,798 A | 10/1980 | Deaton |
| 4,266,545 A | 5/1981 | Moss |
| 4,293,609 A | 10/1981 | Erickson |
| 4,321,020 A | 3/1982 | Mittal |
| 4,331,147 A | 5/1982 | Armstrong |
| 4,538,920 A | 9/1985 | Drake |
| 4,569,674 A | 2/1986 | Phillips et al. |
| 4,578,060 A | 3/1986 | Huck et al. |
| 4,585,397 A | 4/1986 | Crawford et al. |
| 4,604,313 A | 8/1986 | McFarland et al. |
| 4,642,105 A * | 2/1987 | Toter ................ A61M 1/69 604/350 |
| 4,655,754 A | 4/1987 | Richmond et al. |
| 4,753,536 A | 6/1988 | Spehar et al. |
| 4,758,238 A | 7/1988 | Sundblom et al. |
| 4,767,026 A | 8/1988 | Keller et al. |
| 4,767,417 A | 8/1988 | Boehringer et al. |
| 4,771,919 A | 9/1988 | Ernst |
| 4,826,494 A | 5/1989 | Richmond et al. |
| 4,840,770 A | 6/1989 | Walz et al. |
| 4,865,816 A | 9/1989 | Walz et al. |
| 4,870,975 A | 10/1989 | Cronk et al. |
| 4,872,450 A | 10/1989 | Austad |
| 4,979,944 A | 12/1990 | Luzsicza |
| 4,988,344 A | 1/1991 | Reising et al. |
| 4,988,345 A | 1/1991 | Reising |
| 5,010,115 A | 4/1991 | Grisoni |
| 5,064,653 A | 11/1991 | Sessions et al. |
| 5,071,104 A | 12/1991 | Witt et al. |
| 5,080,493 A | 1/1992 | McKown et al. |
| 5,092,858 A * | 3/1992 | Benson ................ A61M 1/68 604/323 |
| 5,135,485 A | 8/1992 | Cohen et al. |
| 5,141,504 A | 8/1992 | Herweck et al. |
| 5,156,602 A | 10/1992 | Steffler |
| 5,246,353 A | 9/1993 | Sohn |
| 5,249,709 A | 10/1993 | Duckworth et al. |
| 5,266,326 A | 11/1993 | Barry et al. |
| 5,333,760 A | 8/1994 | Simmen |
| D352,463 S | 11/1994 | Kubo |
| 5,360,445 A | 11/1994 | Goldowsky |
| 5,386,735 A | 2/1995 | Langdon |
| 5,397,299 A | 3/1995 | Karwoski et al. |
| 5,411,474 A | 5/1995 | Ott et al. |
| 5,424,265 A * | 6/1995 | Weinstein ............. A61M 1/684 210/502.1 |
| 5,456,745 A | 10/1995 | Roreger et al. |
| 5,458,586 A | 10/1995 | Adiletta |
| 5,466,229 A | 11/1995 | Elson et al. |
| 5,484,428 A | 1/1996 | Drainville et al. |
| 5,582,596 A | 12/1996 | Fukunaga et al. |
| 5,583,114 A | 12/1996 | Barrows et al. |
| 5,591,297 A | 1/1997 | Ahr |
| 5,609,271 A | 3/1997 | Keller et al. |
| 5,612,050 A | 3/1997 | Rowe et al. |
| 5,630,855 A | 5/1997 | Lundback |
| 5,636,643 A | 6/1997 | Argenta et al. |
| 5,660,823 A | 8/1997 | Chakrabarti et al. |
| 5,685,214 A | 11/1997 | Neff et al. |
| 5,707,173 A | 1/1998 | Cottone et al. |
| 5,717,030 A | 2/1998 | Dunn et al. |
| 5,747,064 A | 5/1998 | Burnett et al. |
| 5,776,193 A | 7/1998 | Kwan et al. |
| 5,785,700 A | 7/1998 | Olson |
| 5,787,928 A | 8/1998 | Allen et al. |
| 5,807,359 A | 9/1998 | Bemis et al. |
| D400,249 S | 10/1998 | Holubar |
| 5,834,007 A | 11/1998 | Kubota |
| 5,874,500 A | 2/1999 | Rhee et al. |
| 5,876,387 A | 3/1999 | Killian et al. |
| 5,882,743 A | 3/1999 | McConnell |
| 5,945,115 A | 8/1999 | Dunn et al. |
| 5,960,837 A | 10/1999 | Cude |
| 5,962,010 A | 10/1999 | Greff et al. |
| 5,998,472 A | 12/1999 | Berger et al. |
| 6,010,527 A | 1/2000 | Augustine et al. |
| 6,075,177 A | 6/2000 | Bahia et al. |
| 6,099,493 A | 8/2000 | Swisher |
| 6,102,205 A | 8/2000 | Greff et al. |
| 6,142,982 A | 11/2000 | Hunt et al. |
| 6,143,352 A | 11/2000 | Clark et al. |
| 6,165,201 A | 12/2000 | Sawhney et al. |
| 6,168,758 B1 | 1/2001 | Forsberg et al. |
| 6,168,788 B1 | 1/2001 | Wortham |
| 6,214,332 B1 | 4/2001 | Askill et al. |
| 6,252,129 B1 | 6/2001 | Coffee |
| D449,891 S | 10/2001 | Moro |
| 6,352,233 B1 | 3/2002 | Barberich |
| D456,514 S | 4/2002 | Brown et al. |
| 6,391,294 B1 | 5/2002 | Dettmar et al. |
| 6,395,955 B1 | 5/2002 | Roe et al. |
| 6,398,761 B1 | 6/2002 | Bills et al. |
| 6,447,802 B2 | 9/2002 | Sessions et al. |
| 6,458,109 B1 | 10/2002 | Henley et al. |
| 6,468,199 B1 | 10/2002 | Satou et al. |
| 6,486,285 B2 | 11/2002 | Fujita |
| 6,495,127 B1 | 12/2002 | Wallace et al. |
| 6,501,002 B1 | 12/2002 | Roe et al. |
| D469,175 S | 1/2003 | Hall et al. |
| 6,509,031 B1 | 1/2003 | Miller et al. |
| 6,521,251 B2 | 2/2003 | Askill et al. |
| 6,547,255 B1 | 4/2003 | Donaway et al. |
| 6,547,467 B2 | 4/2003 | Quintero |
| D475,132 S | 5/2003 | Randolph |
| 6,575,333 B1 | 6/2003 | Raboin |
| 6,575,940 B1 | 6/2003 | Levinson et al. |
| D477,869 S | 7/2003 | Vijfvinkel |
| 6,596,704 B1 | 7/2003 | Court et al. |
| D478,659 S | 8/2003 | Hall et al. |
| 6,620,379 B1 | 9/2003 | Piuk et al. |
| 6,627,216 B2 | 9/2003 | Brandt et al. |
| D481,459 S | 10/2003 | Nahm |
| 6,629,774 B1 | 10/2003 | Gruendeman |
| 6,723,430 B2 | 4/2004 | Kurata et al. |
| 6,730,299 B1 | 5/2004 | Tayot et al. |
| 6,755,807 B2 | 6/2004 | Risk, Jr. et al. |
| 6,764,462 B2 | 7/2004 | Risk, Jr. et al. |
| 6,790,438 B1 | 9/2004 | Constancis et al. |
| 6,800,074 B2 | 10/2004 | Henley et al. |
| 6,820,483 B1 | 11/2004 | Beckerman |
| 6,856,821 B2 | 2/2005 | Johnson |
| 6,885,116 B2 | 4/2005 | Knirck et al. |
| D504,953 S | 5/2005 | Ryan |
| D516,217 S | 2/2006 | Brown et al. |
| D522,657 S | 6/2006 | Murphy et al. |

(56) References Cited

U.S. PATENT DOCUMENTS

| | | |
|---|---|---|
| 7,066,949 B2 | 6/2006 | Gammons et al. |
| 7,129,210 B2 | 10/2006 | Lowinger et al. |
| 7,153,294 B1 | 12/2006 | Farrow |
| D537,944 S | 3/2007 | Eda et al. |
| 7,198,046 B1 | 4/2007 | Argenta et al. |
| D544,092 S | 6/2007 | Lewis |
| 7,240,676 B2 | 7/2007 | Rutter |
| D548,347 S | 8/2007 | Ichino et al. |
| D551,578 S | 9/2007 | Kuriger et al. |
| 7,303,757 B2 | 12/2007 | Schankereli et al. |
| 7,367,342 B2 | 5/2008 | Butler |
| 7,438,705 B2 | 10/2008 | Karpowicz et al. |
| D580,285 S | 11/2008 | Hendrickson et al. |
| D585,137 S | 1/2009 | Onoda et al. |
| 7,503,910 B2 | 3/2009 | Adahan |
| D593,676 S | 6/2009 | Locke et al. |
| D594,114 S | 6/2009 | Locke et al. |
| 7,569,742 B2 | 8/2009 | Haggstrom et al. |
| D602,583 S | 10/2009 | Pidgeon et al. |
| D602,584 S | 10/2009 | Pidgeon et al. |
| 7,604,610 B2 | 10/2009 | Shener et al. |
| 7,608,066 B2 | 10/2009 | Vogel |
| 7,611,500 B1 | 11/2009 | Lina et al. |
| 7,615,036 B2 | 11/2009 | Joshi et al. |
| 7,625,362 B2 | 12/2009 | Boehringer et al. |
| 7,670,323 B2 | 3/2010 | Hunt et al. |
| 7,700,819 B2 | 4/2010 | Ambrosio et al. |
| 7,722,582 B2 | 5/2010 | Lina et al. |
| D617,094 S | 6/2010 | Pidgeon et al. |
| D617,461 S | 6/2010 | Kaushal et al. |
| 7,731,702 B2 | 6/2010 | Bybordi et al. |
| 7,758,554 B2 | 7/2010 | Lina et al. |
| 7,794,450 B2 | 9/2010 | Blott et al. |
| 7,837,673 B2 | 11/2010 | Vogel |
| D630,313 S | 1/2011 | Pidgeon et al. |
| D630,725 S | 1/2011 | Pidgeon et al. |
| 7,862,831 B2 | 1/2011 | Wang et al. |
| 7,896,823 B2 | 3/2011 | Mangrum et al. |
| 7,910,135 B2 | 3/2011 | St. John et al. |
| 7,927,318 B2 | 4/2011 | Risk, Jr. et al. |
| 7,976,598 B2 | 7/2011 | Matula et al. |
| 7,998,125 B2 | 8/2011 | Weston |
| 8,007,164 B2 | 8/2011 | Miyano et al. |
| 8,021,348 B2 | 9/2011 | Risk, Jr. et al. |
| 8,048,046 B2 | 11/2011 | Hudspeth et al. |
| 8,097,272 B2 | 1/2012 | Addison |
| 8,118,794 B2 | 2/2012 | Weston |
| 8,119,160 B2 | 2/2012 | Looney et al. |
| 8,172,817 B2 | 5/2012 | Michaels et al. |
| 8,226,942 B2 | 7/2012 | Charier et al. |
| 8,235,972 B2 | 8/2012 | Adahan |
| 8,240,470 B2 | 8/2012 | Pidgeon et al. |
| 8,257,327 B2 | 9/2012 | Blott et al. |
| 8,267,909 B2 | 9/2012 | Clementi et al. |
| 8,273,368 B2 | 9/2012 | Ambrosio et al. |
| 8,294,586 B2 | 10/2012 | Pidgeon et al. |
| 8,303,552 B2 | 11/2012 | Weston |
| 8,323,264 B2 | 12/2012 | Weston et al. |
| 8,333,744 B2 | 12/2012 | Hartwell et al. |
| 8,348,910 B2 | 1/2013 | Blott et al. |
| 8,372,049 B2 | 2/2013 | Jaeb et al. |
| 8,410,189 B2 | 4/2013 | Carnahan et al. |
| 8,414,519 B2 | 4/2013 | Hudspeth et al. |
| 8,444,392 B2 | 5/2013 | Turner et al. |
| 8,460,255 B2 | 6/2013 | Joshi et al. |
| 8,494,349 B2 | 7/2013 | Gordon |
| 8,535,296 B2 | 9/2013 | Blott et al. |
| 8,622,981 B2 | 1/2014 | Hartwell et al. |
| 8,753,670 B2 | 6/2014 | Delmotte |
| 8,795,635 B2 | 8/2014 | Tamarkin et al. |
| 8,795,713 B2 | 8/2014 | Makower et al. |
| 8,814,840 B2 | 8/2014 | Evans et al. |
| 8,814,841 B2 | 8/2014 | Hartwell |
| 8,968,773 B2 | 3/2015 | Thomas et al. |
| 8,974,429 B2 | 3/2015 | Gordon et al. |
| 9,028,872 B2 | 5/2015 | Gaserod et al. |
| 9,205,183 B2* | 12/2015 | Hartwell ............. A61M 1/60 |
| 9,211,486 B2 | 12/2015 | Locke et al. |
| 9,320,838 B2 | 4/2016 | Hartwell et al. |
| 9,375,521 B2 | 6/2016 | Hudspeth et al. |
| 9,408,954 B2 | 8/2016 | Gordon et al. |
| 9,561,312 B2 | 2/2017 | Heaton et al. |
| 9,636,440 B2 | 5/2017 | Weston et al. |
| 10,071,190 B2* | 9/2018 | Hartwell ............. A61M 1/60 |
| 2001/0004082 A1 | 6/2001 | Keller et al. |
| 2001/0043913 A1 | 11/2001 | Spaans et al. |
| 2002/0038826 A1 | 4/2002 | Hurray et al. |
| 2002/0122771 A1 | 9/2002 | Holland et al. |
| 2002/0145007 A1 | 10/2002 | Sawhney et al. |
| 2002/0145012 A1 | 10/2002 | Ho |
| 2002/0161346 A1 | 10/2002 | Lockwood et al. |
| 2002/0187182 A1 | 12/2002 | Kramer et al. |
| 2002/0198490 A1 | 12/2002 | Wirt et al. |
| 2003/0040478 A1 | 2/2003 | Drucker et al. |
| 2003/0050594 A1 | 3/2003 | Zamierowski |
| 2003/0069535 A1 | 4/2003 | Shalaby |
| 2003/0101826 A1 | 6/2003 | Neubert |
| 2003/0143189 A1 | 7/2003 | Askill et al. |
| 2003/0163101 A1 | 8/2003 | Say |
| 2003/0181850 A1 | 9/2003 | Diamond et al. |
| 2003/0183653 A1 | 10/2003 | Bills |
| 2003/0212357 A1 | 11/2003 | Pace |
| 2003/0235635 A1 | 12/2003 | Fong et al. |
| 2004/0006321 A1 | 1/2004 | Cheng et al. |
| 2004/0033466 A1 | 2/2004 | Shellard et al. |
| 2004/0037897 A1 | 2/2004 | Benjamin et al. |
| 2004/0049187 A1 | 3/2004 | Burnett et al. |
| 2004/0073152 A1 | 4/2004 | Karason et al. |
| 2004/0087918 A1 | 5/2004 | Johnson, III et al. |
| 2004/0153029 A1 | 8/2004 | Blischak et al. |
| 2004/0167482 A1 | 8/2004 | Watson |
| 2004/0167617 A1 | 8/2004 | Voellmicke et al. |
| 2004/0171998 A1 | 9/2004 | Marasco, Jr. |
| 2004/0180093 A1 | 9/2004 | Burton et al. |
| 2004/0233631 A1 | 11/2004 | Lord |
| 2005/0137539 A1* | 6/2005 | Biggie ............... A61M 1/98 |
| | | 604/313 |
| 2005/0144711 A1 | 7/2005 | Valadez et al. |
| 2005/0166683 A1 | 8/2005 | Krivitski et al. |
| 2005/0230422 A1 | 10/2005 | Muller et al. |
| 2005/0248045 A1 | 11/2005 | Anthony |
| 2006/0059980 A1 | 3/2006 | Matsubara et al. |
| 2006/0079599 A1 | 4/2006 | Arthur |
| 2006/0129137 A1 | 6/2006 | Lockwood et al. |
| 2006/0173514 A1 | 8/2006 | Biel et al. |
| 2006/0253082 A1 | 11/2006 | McIntosh et al. |
| 2006/0273109 A1 | 12/2006 | Keller |
| 2006/0280650 A1 | 12/2006 | Wong et al. |
| 2007/0004896 A1 | 1/2007 | Ito et al. |
| 2007/0009580 A1 | 1/2007 | DiCosmo et al. |
| 2007/0021697 A1 | 1/2007 | Ginther et al. |
| 2007/0055209 A1 | 3/2007 | Patel et al. |
| 2007/0118096 A1 | 5/2007 | Smith et al. |
| 2007/0135779 A1 | 6/2007 | Lalomia et al. |
| 2007/0141101 A1 | 6/2007 | Nugent et al. |
| 2007/0147947 A1 | 6/2007 | Stenton et al. |
| 2007/0164047 A1 | 7/2007 | Reidt et al. |
| 2007/0185463 A1 | 8/2007 | Mulligan |
| 2007/0186404 A1 | 8/2007 | Drew et al. |
| 2007/0203062 A1 | 8/2007 | Ellis-Behnke et al. |
| 2007/0219532 A1 | 9/2007 | Karpowicz et al. |
| 2007/0219535 A1 | 9/2007 | Phung et al. |
| 2008/0004549 A1 | 1/2008 | Anderson et al. |
| 2008/0011667 A1 | 1/2008 | Ruschke |
| 2008/0033400 A1 | 2/2008 | Holper et al. |
| 2008/0060550 A1 | 3/2008 | Macdonald et al. |
| 2008/0082059 A1* | 4/2008 | Fink ............... A61M 1/60 |
| | | 604/305 |
| 2008/0089173 A1 | 4/2008 | Lu et al. |
| 2008/0125698 A1 | 5/2008 | Gerg et al. |
| 2008/0183233 A1 | 7/2008 | Koch et al. |
| 2008/0206155 A1 | 8/2008 | Tamarkin et al. |
| 2008/0208163 A1 | 8/2008 | Wilkie |
| 2008/0254103 A1 | 10/2008 | Harris et al. |

(56) References Cited

U.S. PATENT DOCUMENTS

| | | |
|---|---|---|
| 2008/0281281 A1 | 11/2008 | Meyer et al. |
| 2008/0287880 A1 | 11/2008 | Keller |
| 2008/0314929 A1 | 12/2008 | Keller |
| 2009/0020561 A1 | 1/2009 | Keller |
| 2009/0022779 A1 | 1/2009 | Kelly et al. |
| 2009/0030086 A1 | 1/2009 | Eady et al. |
| 2009/0093550 A1 | 4/2009 | Rolfes et al. |
| 2009/0098073 A1 | 4/2009 | Macdonald et al. |
| 2009/0099519 A1 | 4/2009 | Kaplan |
| 2009/0134186 A1 | 5/2009 | Keller |
| 2009/0157016 A1 | 6/2009 | Adahan |
| 2009/0157017 A1 | 6/2009 | Ambrosio |
| 2009/0196844 A1 | 8/2009 | Choi et al. |
| 2009/0204049 A1 | 8/2009 | Lee |
| 2009/0240218 A1 | 9/2009 | Braga et al. |
| 2009/0254066 A1 | 10/2009 | Heaton et al. |
| 2009/0275872 A1 | 11/2009 | Addison et al. |
| 2009/0299251 A1 | 12/2009 | Buan |
| 2009/0299306 A1 | 12/2009 | Buan |
| 2009/0312725 A1 | 12/2009 | Braga |
| 2009/0326488 A1* | 12/2009 | Budig .................. A61M 1/966 604/319 |
| 2010/0030132 A1 | 2/2010 | Niezgoda et al. |
| 2010/0036305 A1 | 2/2010 | Green |
| 2010/0069850 A1 | 3/2010 | Fabo |
| 2010/0230467 A1 | 9/2010 | Criscuolo et al. |
| 2011/0021431 A1 | 1/2011 | Jones et al. |
| 2011/0033503 A1 | 2/2011 | Sinko et al. |
| 2011/0086077 A1 | 4/2011 | McCrea et al. |
| 2011/0087178 A2 | 4/2011 | Weston |
| 2011/0112493 A1 | 5/2011 | Koch et al. |
| 2011/0130712 A1 | 6/2011 | Topaz |
| 2011/0275964 A1 | 11/2011 | Greener |
| 2011/0313375 A1 | 12/2011 | Michaels |
| 2012/0035560 A1 | 2/2012 | Eddy et al. |
| 2012/0046626 A1 | 2/2012 | Sanders et al. |
| 2012/0265160 A1 | 10/2012 | Wiesner |
| 2013/0144235 A1 | 6/2013 | Augustine et al. |
| 2014/0163491 A1 | 6/2014 | Schuessler et al. |
| 2014/0207091 A1 | 7/2014 | Heagle et al. |
| 2014/0320283 A1 | 10/2014 | Lawhorn |
| 2015/0165101 A1 | 6/2015 | Blott et al. |
| 2015/0343122 A1 | 12/2015 | Hartwell |
| 2016/0184498 A1 | 6/2016 | Jaeb et al. |
| 2016/0325025 A1 | 11/2016 | Hudspeth et al. |
| 2016/0331877 A1 | 11/2016 | Braga et al. |
| 2017/0281424 A1 | 10/2017 | Fink et al. |
| 2018/0104387 A1 | 4/2018 | Braga et al. |
| 2020/0171217 A9 | 6/2020 | Braga et al. |

FOREIGN PATENT DOCUMENTS

| | | |
|---|---|---|
| DE | 4312852 A1 | 10/1993 |
| DE | 102007063294 A1 | 7/2009 |
| EP | 0358302 A2 | 3/1990 |
| EP | 0521434 A1 | 1/1993 |
| EP | 0858810 A2 | 8/1998 |
| EP | 0888141 A1 | 1/1999 |
| EP | 1007015 A1 | 6/2000 |
| EP | 1029585 A1 | 8/2000 |
| EP | 1105171 A2 | 6/2001 |
| EP | 1105180 A1 | 6/2001 |
| EP | 1107813 A1 | 6/2001 |
| EP | 1030657 B1 | 10/2001 |
| EP | 1306123 A1 | 5/2003 |
| EP | 1440737 A1 | 7/2004 |
| EP | 2223711 A1 | 9/2010 |
| EP | 2248546 A2 | 11/2010 |
| FR | 1163907 A | 10/1958 |
| GB | 1415096 A | 11/1975 |
| GB | 2288734 A | 11/1995 |
| GB | 2418738 A | 4/2006 |
| GB | 2424582 A | 10/2006 |
| GB | 2435419 A | 8/2007 |
| JP | 2000202022 A | 7/2000 |
| WO | WO-8700439 A1 | 1/1987 |
| WO | WO-9209301 A1 | 6/1992 |
| WO | WO-9209651 A1 | 6/1992 |
| WO | WO-9306802 A1 | 4/1993 |
| WO | WO-9309176 A2 | 5/1993 |
| WO | WO-9420133 A1 | 9/1994 |
| WO | WO-9605873 A1 | 2/1996 |
| WO | WO-9640174 A1 | 12/1996 |
| WO | WO-9703717 A1 | 2/1997 |
| WO | WO-9733922 A1 | 9/1997 |
| WO | WO-9742986 A1 | 11/1997 |
| WO | WO-9806444 A1 | 2/1998 |
| WO | WO-9917698 A1 | 4/1999 |
| WO | WO-9930629 A1 | 6/1999 |
| WO | WO-9947097 A2 | 9/1999 |
| WO | WO-9965536 A1 | 12/1999 |
| WO | WO-0038752 A1 | 7/2000 |
| WO | WO-0061206 A1 | 10/2000 |
| WO | WO-0062827 A2 | 10/2000 |
| WO | WO-0064396 A1 | 11/2000 |
| WO | WO-0162312 A1 | 8/2001 |
| WO | WO-0166017 A1 | 9/2001 |
| WO | WO-0202079 A1 | 1/2002 |
| WO | WO-02094256 A1 | 11/2002 |
| WO | WO-02102864 A1 | 12/2002 |
| WO | WO-03022333 A1 | 3/2003 |
| WO | WO-03053346 A2 | 7/2003 |
| WO | WO-03101508 A2 | 12/2003 |
| WO | WO-2004054632 A1 | 7/2004 |
| WO | WO-2005017000 A1 | 2/2005 |
| WO | WO-2005018695 A1 | 3/2005 |
| WO | WO-2005105175 A1 | 11/2005 |
| WO | WO-2005105176 A1 | 11/2005 |
| WO | WO-2005105179 A1 | 11/2005 |
| WO | WO-2005118011 A1 | 12/2005 |
| WO | WO-2006014534 A2 | 2/2006 |
| WO | WO-2006030054 A1 | 3/2006 |
| WO | WO-2006034128 A2 | 3/2006 |
| WO | WO-2006052745 A2 | 5/2006 |
| WO | WO-2006135506 A2 | 12/2006 |
| WO | WO-2007031757 A1 | 3/2007 |
| WO | WO-2007087808 A1 | 8/2007 |
| WO | WO-2007087809 A1 | 8/2007 |
| WO | WO-2007106594 A2 | 9/2007 |
| WO | WO-2007124198 A2 | 11/2007 |
| WO | WO-2008039314 A2 | 4/2008 |
| WO | WO-2008048481 A2 | 4/2008 |
| WO | WO-2008076407 A2 | 6/2008 |
| WO | WO-2008082444 A2 | 7/2008 |
| WO | WO-2008134544 A1 | 11/2008 |
| WO | WO-2008134774 A2 | 11/2008 |
| WO | WO-2009002260 A1 | 12/2008 |
| WO | WO-2009004289 A2 | 1/2009 |
| WO | WO-2009042514 A1 | 4/2009 |
| WO | WO-2009052193 A1 | 4/2009 |
| WO | WO-2009060327 A2 | 5/2009 |
| WO | WO-2009077722 A1 | 6/2009 |
| WO | WO-2009086580 A1 | 7/2009 |
| WO | WO-2009111655 A2 | 9/2009 |
| WO | WO-2009145703 A1 | 12/2009 |
| WO | WO-2009151645 A2 | 12/2009 |
| WO | WO-2010039481 A1 | 4/2010 |

OTHER PUBLICATIONS

Fong K.D., et al., "SNaP Wound Care System: Ultraportable Mechanically Powered Negative Pressure Wound Therapy," Advances in Wound Care, vol. 1(1), Feb. 2012, 4 pages.

International Preliminary Report on Patentability for Application No. PCT/GB2009/050200, mailed on Sep. 10, 2010, 8 pages.

International Search Report for Application No. PCT/GB2009/050200, mailed on Jun. 5, 2009, 3 pages.

KCI, "V.A.C. Freedom User's Guide," May 2002, 16 pages.

Mitchell R.N., et al., "Role of Stem Cells in Tissue Homeostasis," Pocket Companion to Robbins and Cotran Pathologic Basis of Disease, 7th Edition, 2006, p. 55 (3 pages).

(56) References Cited

OTHER PUBLICATIONS

The Free Dictionary, "Evaporation," The American Heritage®, Science Dictionary, 2005, 3 pages.

* cited by examiner

FLUID COLLECTION

CROSS-REFERENCE TO RELATED APPLICATIONS

This application is a continuation of U.S. application Ser. No. 16/118,198, filed Aug. 30, 2018, which is a continuation of U.S. application Ser. No. 14/948,117, filed Nov. 20, 2015, now U.S. Pat. No. 10,071,190, which is a continuation of U.S. application Ser. No. 12/918,202, filed Mar. 28, 2011, now U.S. Pat. No. 9,205,183, which is a U.S. National Phase of the PCT International Application No. PCT/GB2009/050200 filed on Feb. 27, 2009, designating the United States and published on Sep. 3, 2009 as WO 2009/106895, and which claims priority to Great Britain Patent Application No. 0803564.4, filed Feb. 27, 2008.

BACKGROUND OF THE INVENTION

Field of the Invention

The present invention relates to a method and apparatus for trapping and collecting fluid. In particular, but not exclusively, the present invention provides an apparatus which can trap and store fluid removed as part of a medical procedure.

Suction pumps are sometimes used in the removal of fluid in medical procedures, for example, during topical negative pressure (TNP) wound therapy, closed suction, surgery and clearance of fluid from lungs etc. During pumping liquid such as wound exudate must be trapped and stored. Fluid traps for such suction pumps thus tend to be bulky even when empty since the container used to trap and collect fluid needs to be of a size suitably big to be useful over a period of time. The bulky fluid traps are not only costly to transport and manufacture but also are difficult to store. Also the relatively large size makes the containers difficult to conceal during use which may provide unsatisfactory to a user trying to carry on their normal life.

Current vacuum pump devices for wound drainage and negative pressure wound therapy (NPWT) often utilise bulky fluid collection canisters to trap the fluid removed from the body. Two types of fluid collection canister are well known, namely rigid canisters formed from a single wall rigid construction and so-called flexible canisters that sit inside a further rigid container. In these latter canisters the inner flexible container is disposable but a relatively large outer rigid body is still needed to protect and support the flexible container and this is prone to the problems noted above.

Summary of Some Exemplifying Embodiments

It is an aim of the present invention to at least partly mitigate the above-mentioned problems.

It is an aim of embodiments of the present invention to provide apparatus which can trap and store fluid and which, when empty, is relatively small and discreet and yet which can expand to provide adequate capacity for the apparatus to be used over a prolonged period of time or when large quantities of liquid are generated.

It is an aim of embodiments of the present invention to provide a method and apparatus for trapping and collecting wound exudate from a wound or fluid from lungs during a medical procedure.

It is an aim of embodiments of the present invention to provide a method of trapping and collecting fluid utilising an expandable container which is able to absorb liquid under compression conditions. Even, for some embodiments, at compression pressures of up to 200 mmHg.

According to a first aspect of the present invention there is provided apparatus for collecting fluid, comprising:
  a body portion comprising a fluid inlet and an outlet;
  an expandable container secured to the body portion;
  at least one wicking element extending from within the body portion into the container; and
  at least one super absorber element arranged inside the container.

According to a second aspect of the present invention there is provided a method for collecting fluid, comprising the steps of:
  applying a negative pressure at an outlet of an apparatus body portion to thereby draw liquid through an inlet of the body portion;
  via at least one wicking element, trapping and transporting the drawn liquid away from the body portion into an expandable container secured to the body portion; and
  absorbing the liquid in the container via at least one super absorber element, the container expanding as the super absorber expands.

Embodiments of the present invention provide a relatively small and compact apparatus and method for using the apparatus which is able to trap and collect fluid. Advantageously, but not exclusively, embodiments of the present invention can be used to trap and collect fluids removed during a medical procedure such as TNP, surgery or the like.

Embodiments of the present invention utilise a wicking material which receives liquid at one location close to an inlet to a body portion. The wicking material rapidly transports the liquid, via capillary action, to a super absorbent material which expands as more and more liquid is absorbed. A flexible and enlargeable container is utilised which expands as the super absorber material absorbs more and more liquid. The wicking material and super absorber prevent collapse of the container when a negative pressure is applied.

Embodiments of the present invention provide a flexible waste container which allows the apparatus to be accommodated on a person in a more user friendly manner. In an "empty" state the waste receptacle is significantly smaller in volume than an equivalent rigid container of fixed initial volume. This reduces transport and storage requirements and reduces the volume in use. This is particularly advantageous as it will be appreciated that conventional canisters used for trapping and containing fluids spend a majority of their life in use in an empty/part empty state.

BRIEF DESCRIPTION OF THE DRAWINGS

Embodiments of the present invention will now be described hereinafter, by way of example only, with reference to the accompanying drawings in which.

Detailed Description of Some Exemplifying Embodiments

Figure 1:
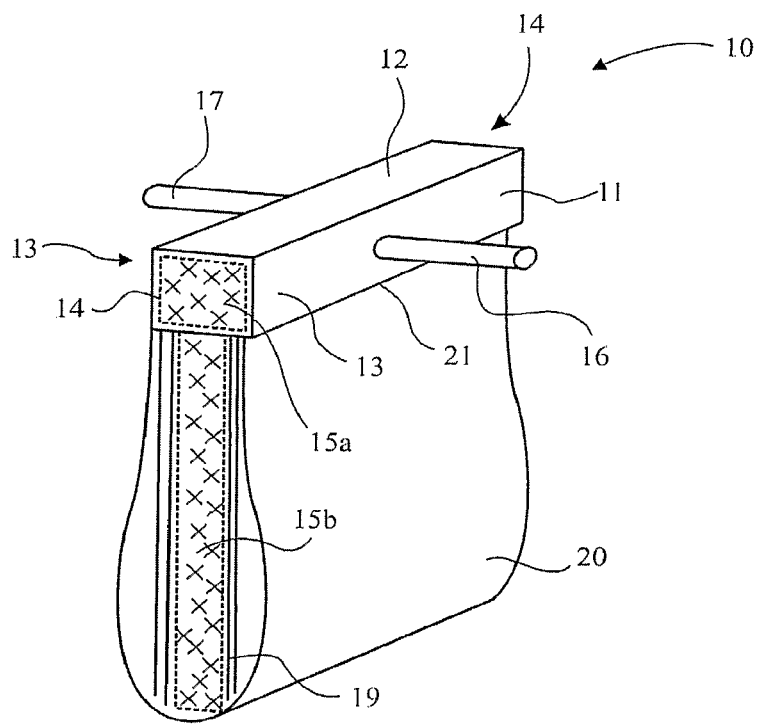
FIG. 1 illustrates apparatus for collecting fluid.

FIG. 1 illustrates a fluid trap 10 according to an embodiment of the present invention. Throughout this specification reference is made to the trapping and holding or storing of fluid. It is to be understood that the trapping process encapsulates the concept of at least partially removing fluid from a flow path whilst the storing/containing aspect refers to the storage of trapped fluid, again away from a fluid path. As illustrated in FIG. 1 the apparatus 10 includes an upper body 11 which is rigid or semi-rigid and may be formed from metal or a plastics material or the like. As illustrated in FIG. 1, the body 11 is a box-like container formed as a paralleliped with an upper substantially rectangular side wall 12 and rectangular side walls 13. Substantially square side walls 14 close the open ends of the paralleliped. It is to be noted that other shapes may be adopted for the body in accordance with further embodiments of the present invention.

It is also to be noted that the front end 14 shown in FIG. 1 is shown cut away to reveal how a mass of wicking material 15 is used to fill the inside of the box-like body 11.

The wicking material 15 includes an upper portion 15a which fills the inside of the body 11 and an elongate portion 15b extending downwardly from the upper portion. The wicking material forming the upper and lower parts of the wick can be formed from any material which may be used to transport liquid via capillary action. For example, cotton gauze, non-woven polyester or the like. A fluid inlet 16 and fluid outlet 17 are provided in the body 11. The fluid inlet 16 allows fluid, from a target location where fluid is to be removed, to be drawn into the fluid trap 10. The fluid outlet 17 is utilised to remove a gaseous part of the input fluid when a negative pressure, provided by a pump or the like, is applied. Effectively fluid is thus sucked through the fluid inlet and outlet. The upper portion of the wicking material 15 is used to trap the liquid part of the pumped fluid and capillary action draws the trapped liquid away from the body 11 in a downwardly direction. The liquid is absorbed by super absorbent material 19 formed as sheets in the dry state. It will be appreciated that in the dry state the superabsorber may alternatively or additionally be provided in a powdered or granular form. A flexible container 20 is sealed at its upper edge 21 to a lower region of the fluid trap body 11. The flexible container 20 can expand as more and more liquid is absorbed by the super absorber 19 during fluid removal. Thus in an initial dry state prior to fluid removal the overall apparatus is relatively small and compact. This makes the apparatus easy to store and transport.

Figure 2:
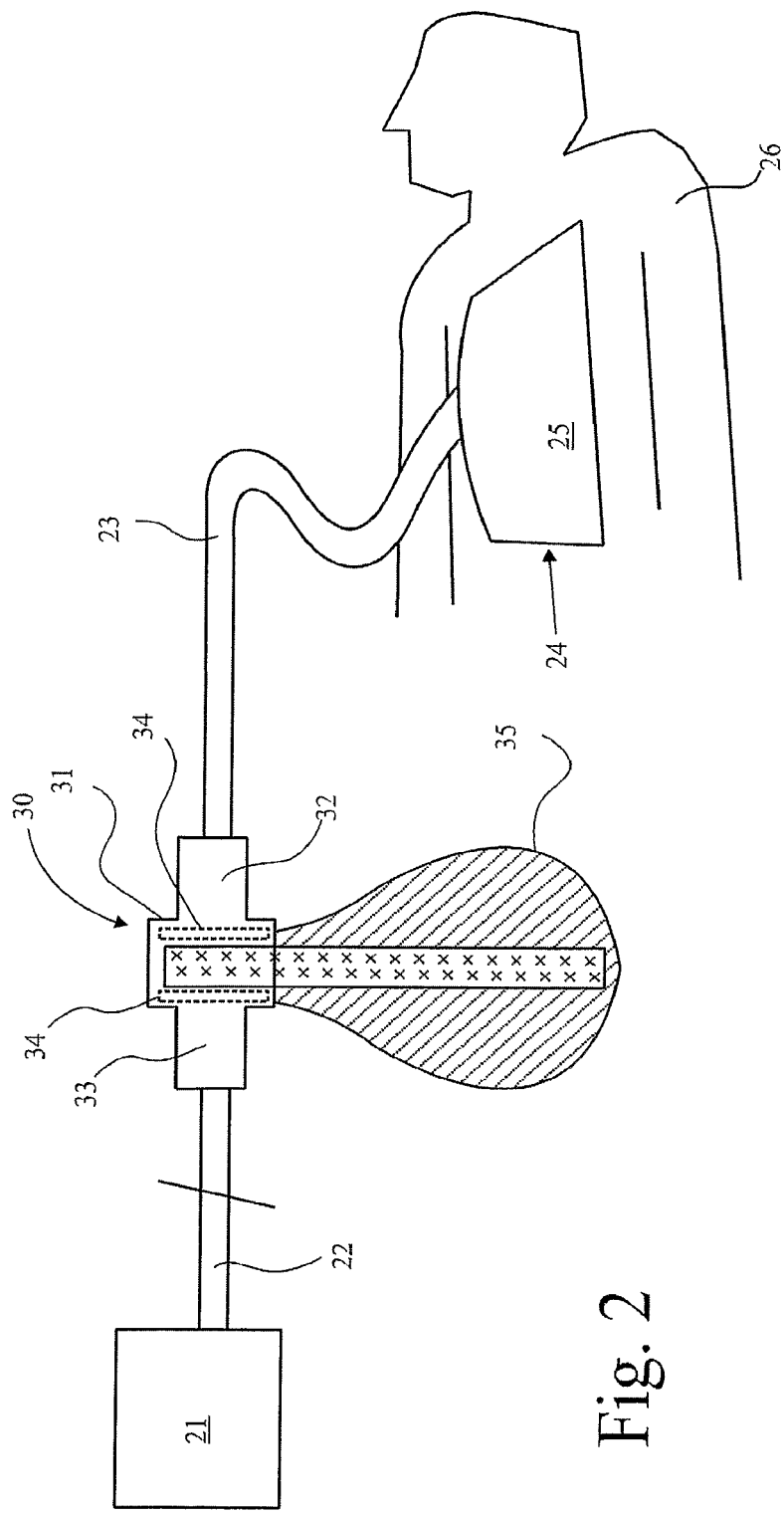
FIG. 2 illustrates apparatus being used during an NPWT procedure.
  In the drawings like reference numerals refer to like parts.

FIG. 2 illustrates an alternative embodiment of the present invention in use during a negative wound pressure therapy (NPWT) process. It is to be understood that embodiments of the present invention are broadly applicable to procedures where a discreet fluid trap and container are required. This may include, but is not restricted to, further medical procedures such as surgery, clearance of fluid from lungs or the like. Embodiments of the present invention are applicable to non-medical uses.

As illustrated in FIG. 2 a pump 21 is connected to a fluid apparatus by a pipe or tube 22 of a desired length. A further pipe or tube 23 connects the fluid trap to a target site such as a wound site 24 aptly covered by a drape 25. During a negative pressure wound therapy treatment the pump 21 continually sucks so as to apply a negative pressure at the wound site 24. The negative pressure is well known to aid healing of a wound of a user 26.

As illustrated in FIG. 2 a fluid trap 30 according to an embodiment of the present invention is located in the flow path between the pump 21 and wound site 24. The fluid trap includes a rigid body 31 which includes a fluid inlet 32 and fluid outlet 33. The fluid flowing through the inlet 32 includes a liquid and gaseous component. The fluid trap 30 traps and stores the liquid part of the input fluid whilst a remaining gaseous component is transferred through the outlet 33 to the pump and may be output via suitable filters or the like from the pump.

Unlike the embodiment illustrated with respect to FIG. 1 a screen 34 is incorporated within the body 31 to prevent migration of the super absorber material from within the flexible container 20 to the inlet or outlet. As such the upper portion of the wick 15 does not need to fill the inside of the body 31.

As illustrated in FIG. 2, during operation liquid flowing along the flow path from the target wound site 24 and pipe 23 is input into the fluid trap. The liquid contacts the upper portion of the wick 15 which transports the liquid downwardly by capillary action away from the flow path and into contact with the super absorber material stored between the wick and the inner surface of the flexible container 35. The super absorber which may be any suitable material, such as, for example, those based on polycationic or polyanionic polymers or the like is able to absorb large volumes of water with respect to dry volume of the material. Suitable superabsorbent polyanionic polymers include, but are not restricted to, polyacrylic acid salts and polyacid derivatives of polysaccharides, such as carboxyalkylcellulose, or structural derivatives. Preferably, when the material is polyanionic, it may be a polyacrylic acid salt or derivative or carboxymethylcellulose or derivative. Preferably, when the material is polycationic, it may be chitosan-based, more preferably a carboxyalkylchitosan or derivative, even more preferably carboxymethylchitosan.

Aptly suitable compositions of matter from which superabsorber can be formed are those comprised, entirely or in part, of high average molecular weight cationic polymers including zwitterionic (carrying both anionic and cationic charge) polymers with a cationic charge bias. The cationic polymer may be, or may be a derivative of, a synthetic or a naturally occurring polymer. Preferably, the cationic polymer is one carrying amine functionality. More preferably, the cationic polymer is a polysaccharide. More preferably still, the cationic polymer is chitosan or a derivative of chitosan. The chitosan may be derived from any source, marine or fungal, and is preferably of a weight average molecular weight (Mw) exceeding 10 kDa (kilodaltons), more preferably exceeding 100 kDa and most preferably exceeding 200 kDa.

Where the polymer is a derivative of chitosan, it is preferably a carboxylated derivative. More preferably, it is a carboxyalkyl derivative of chitosan. More preferably still, it is a carboxymethyl derivative of chitosan. The carboxymethyl derivative of chitosan is preferably of a weight average molecular weight exceeding 50 kDa, more preferably exceeding 100 kDa and most preferably exceeding 500 kDa.

Notably, the super absorbers are able to absorb under compression even at compression pressures of up to 200 mmHg. Thus, as the material absorbs the fluid it is able to expand in volume within the flexible container and counteract the force on the flexible container generated as a result of the interior being under partial vacuum and the exterior having the pressure of the atmosphere acting upon it.

According to embodiments of the present invention the expandable container 20, 35 may be a flexible bag. However, alternative expandable containers are envisaged according to further embodiments of the present invention.

Embodiments of the present invention obviate the need for a bulky rigid waste canister and replaces such a canister with a flexible bag or other such receptacle of only relatively small volume when empty. In order to prevent the bag completely collapsing under vacuum the bag contains wicking material and super absorbent material such that the sides of the bag are not able to wholly collapse and touch together. Thus, when operating under vacuum, fluid can enter the bag from a wound site and come into contact with the wicking material e.g. cotton gauze, non-woven polyester or the like. Liquid is trapped by the wicking layer and then rapidly transported via capillary action to the super absorbent material e.g. those noted above or the like. It is to be noted that if a puncture occurs to the expandable container the super absorbent material is such that the expandable container leaks air rather than any liquid which remains within the super absorber. This ensures the fluid trap remains hygienic.

According to embodiments of the present invention, the flexible bag may aptly have a pathogen filter on the exit port and/or a valve on the inlet port to improve control of pathogens during operation of the drainage system. In order to prevent the ports from becoming blocked before the bag is full of liquid the super absorber is prevented from migration to the port by ensuring that the rigid body is substantially full of wicking material or by the inclusion of screens around the port regions.

Embodiments of the present invention provide for a flexible waste container allowing it to be accommodated on a person in a more user friendly manner. The empty state of the waste receptacle is significantly smaller in volume (typically 10 times smaller) than an equivalent rigid container of fixed initial volume. The apparatus is thus smaller and lighter thus reducing transport and storage requirements and reducing the volume in use.

It is to be noted that the super absorber can continue to absorb and thus expand despite the negative internal pressure provided by the pump.

Throughout the description and claims of this specification, the words "comprise" and "contain" and variations of the words, for example "comprising" and "comprises", means "including but not limited to", and is not intended to (and does not) exclude other moieties, additives, components, integers or steps.

Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith.

What is claimed is:

1. A fluid collection system for use with negative pressure wound therapy for collecting fluid from a wound site, the system comprising:
   a canister comprising an inlet, an outlet, and a container, wherein the canister comprise a top portion and a bottom portion and a length extending from the top portion to the bottom portion, the inlet and outlet at the top portion of the canister, the inlet adapted to be in fluid communication with a wound dressing at the wound site, the outlet adapted to be in fluid communication with a negative pressure source, and the container configured to be expandable and in fluid communication with the inlet and the outlet;
   a wicking material disposed within the container; and
   a plurality of sheets of absorptive material disposed within the container, wherein the plurality of sheets of absorptive material extend from the top portion to the bottom portion of the canister;
   wherein the wicking material is configured to transport fluid to the plurality of sheets of absorptive material.

2. The system as in claim 1, further comprising a first conduit configured to fluidically connect the inlet of the canister with a wound dressing and a second conduit configured to fluidically connect the outlet of the canister with a source of negative pressure.

3. The system as in claim 1, the canister further comprising a first side and a second side, wherein the inlet is configured to be in fluid communication with a wound dressing and is located on the top portion of the first side of the canister and the outlet is configured to be in fluid communication with a negative pressure source, the outlet located on the top portion of the second side of the canister.

4. The system as in claim 1, wherein the plurality of sheets of absorptive material are oriented within the container essentially parallel to a first surface of the container, the wicking material and the plurality of sheets of absorptive material are positioned wherein at least one sheet of absorptive material is in fluid communication with the wicking material.

5. The system as in claim 1, wherein the container is configured to expand as fluid is absorbed by the plurality of sheets of absorptive material.

6. A method for expanding a fluid collection apparatus, the method comprising:
   introducing fluid from a wound into a canister, the canister comprising a container, wherein the canister comprise an inlet, an outlet, a top portion, and a bottom portion and a length extending from the top portion to the bottom portion, the inlet and outlet at the top portion of the canister, the container containing a plurality of sheets of absorptive material within the container configured to retain fluid from the wound, and a wicking material within the container configured to transport fluid to the plurality of sheets of absorptive material, wherein the plurality of sheets extend from the top portion to the bottom portion of the canister; and
   expanding the container wherein the container is configured to expand as fluid is absorbed by the plurality of sheets of absorptive material.

7. A fluid collection system for collecting fluids from a wound site using reduced pressure, the fluid collection system comprising:
   a container for receiving and collecting fluids from the wound site, the container configured to be expandable, wherein the container comprises an inlet, an outlet, a top portion, and a bottom portion and a length extending from the top portion to the bottom portion, the inlet and outlet at the top portion of the container;
   a plurality of sheets of absorptive material within the container, wherein the plurality of sheets extend from the top portion to the bottom portion of the container; and
   a wicking material positioned within the container, wherein the wicking material is configured to transport fluid to a surface of the plurality of sheets of absorptive material.

* * * * *